US009446326B2

(12) United States Patent
Walker

(10) Patent No.: US 9,446,326 B2
(45) Date of Patent: Sep. 20, 2016

(54) METHOD AND APPARATUS FOR ETHANOL PRODUCTION

(71) Applicant: Dx Resources LLC, Tampa, FL (US)

(72) Inventor: David Walker, Clearwater, FL (US)

(73) Assignee: DX RESOURCES LLC, Tampa, FL (US)

( * ) Notice: Subject to any disclaimer, the term of this patent is extended or adjusted under 35 U.S.C. 154(b) by 365 days.

(21) Appl. No.: 14/192,957

(22) Filed: Feb. 28, 2014

(65) Prior Publication Data

US 2014/0174904 A1    Jun. 26, 2014

Related U.S. Application Data

(63) Continuation of application No. PCT/US2012/053324, filed on Aug. 31, 2012.

(60) Provisional application No. 61/529,365, filed on Aug. 31, 2011.

(51) Int. Cl.
| | |
|---|---|
| *C07C 29/80* | (2006.01) |
| *C07C 13/08* | (2006.01) |
| *B01D 3/06* | (2006.01) |
| *B01D 3/00* | (2006.01) |

(52) U.S. Cl.
CPC ............ *B01D 3/065* (2013.01); *B01D 3/002* (2013.01); *C07C 29/80* (2013.01); *Y02P 20/57* (2015.11)

(58) Field of Classification Search
CPC ....... C07C 29/80; C07C 31/08; B01D 3/002; B01D 3/065; Y02P 20/57
USPC ..................................... 203/19; 202/81, 174
See application file for complete search history.

(56) References Cited

U.S. PATENT DOCUMENTS

| | | | |
|---|---|---|---|
| 7,572,353 B1 | 8/2009 | Vander Griend | |
| 2002/0069987 A1 | 6/2002 | Pye | |
| 2009/0176289 A1 | 7/2009 | Friedmann | |
| 2010/0055239 A1* | 3/2010 | De Almeida | B01D 3/002 426/31 |
| 2010/0196979 A1 | 8/2010 | Brikmire et al. | |
| 2011/0230394 A1* | 9/2011 | Wiatr | A01N 31/02 514/2.4 |
| 2014/0311889 A1* | 10/2014 | Zaher | B01D 3/002 203/42 |

FOREIGN PATENT DOCUMENTS

WO    88/02649 A1    4/1988

\* cited by examiner

*Primary Examiner* — Frank Lawrence
(74) *Attorney, Agent, or Firm* — Boyle Fredrickson, S.C.

(57) ABSTRACT

An integrated bioethanol production and evaporation process and system produce reduces high quality ethanol and concentrated stillage. The process and system provide a significant energy savings over conventional bioethanol production and evaporation systems by using the energy ("vapor") that drives the distillation process to also drive a multiple effect evaporator, preferably a multiple effect TASTE™ evaporator to "flash" or vaporize alcohol from the distillate. Additional energy savings are provided by passing fermented material through one or more pre-heaters of the multiple effect evaporator to increase the temperature of the fermented material prior to its distillation. The system preferably includes a pre-flash evaporator upstream of an alcohol recovery assembly in the direction of vapor flow and a multi-effect post-flash evaporator downstream of the alcohol recovery assembly.

19 Claims, 2 Drawing Sheets

METHOD AND APPARATUS FOR ETHANOL PRODUCTION

CROSS-REFERENCE TO RELATED APPLICATIONS

This is a continuation of International Patent Application Ser. No. PCT/US2012/053324, filed Aug. 31, 2012, which claims priority on U.S. Provisional Patent Application Ser. No. 61/529,365, filed Aug. 31, 2011, both entitled *Method and Apparatus for Ethanol Production* and both filed in the name of the present inventor.

BACKGROUND OF THE INVENTION

1. Field of the Invention

The present invention relates to processing of fermented feedstock and, more particularly, a method and apparatus for producing bioethanol, concentrated stillage, and pure water.

2. Discussion of the Related Art

Ethanol (ethyl alcohol) is commonly used in the United States, Brazil, and other countries as a biofuel additive for gasoline and for other purposes. In the United States, for example, motor fuel or gasoline for automobiles will often contain up to ten percent ethanol. In Brazil, the concentration of ethanol is typically from two percent to ninety percent. A small percentage of global production of ethanol is derived, from petroleum, with the overwhelming majority of ethanol being produced from feedstock, such as corn, sugar cane, sugar beet, sorghum, switchgrass, barley, potatoes, sweet potatoes, fruit, molasses, grain, and wheat. Ethanol that is produced from feedstock is commonly referred to as "bioethanol."

Bioethanol is produced from fermented feedstock and, more particularly, from microbial fermentation of sugars contained in the feedstock. In the case of corn-based bioethanol, the corn is first "mashed" to break the corn starch down to sugars before being exposed to the microbial fermentation process. Mashing is not required for sugar cane, sweet sorghum and other feedstock that are high in natural sugar content. In either event, the fermented material is then distilled to remove its water content, thus providing essentially water-free (near 200 proof) ethanol that can be used, e.g., as a gasoline additive. Specifically, the fermented mixture, sometimes called "beer" or "Vanessa", is pumped to a distillation system and heated. The differences in the boiling points of ethanol and water (78° C. or 172° F. for ethanol vs. 100° C. or 212° F. for water) are used to boil off and separate the ethanol. The ethanol vapor will typically contain approximately five percent water. To further reduce the water content, the ethanol vapor is condensed and passed through a sieve to yield near 200 proof, waterless ethanol.

In addition to producing ethanol, as described above, one of the byproducts of the distillation process is a heavily watered distillate known generally as "stillage" or "stillbottoms". The stillage is composed of insolubles, i.e., solids from the feedstock and yeast added for fermentation, and liquid from the water added during the process. The insolubles are generally nutrient rich and can be used for fertilizer, livestock dressing, and the like. Most of these applications require significant dewatering of the initial or "thin" stillage to produce "concentrated stillage" that has a solids content of on the order of 25% to 65% or higher. About 85% of the total stillage volume typically is removed from the stillage during this dewatering. Some applications require essentially complete dewatering and other post-processing of the concentrated stillage.

Stillage dewatering efforts have included mechanical separators, sieves and screens, and more recently, evaporators. As their name suggest, mechanical separators are designed to mechanically separate the insolubles from the water. Numerous separator designs have been developed, but their success has been limited. One of the principle drawbacks of mechanical separators and similar systems that are based on screens and sieves is that copious volumes of water must be pumped through the dewatering system. For example, it is not uncommon for a bioethanol production plant to pump 280,000 or more pounds of thin stillage per hour through its dewatering system. Needless to say, moving that much stillage and water, at that rate, requires a tremendous amount of energy.

SUMMARY OF THE INVENTION

The present invention is directed to an integrated bioethanol production and evaporation associated process that produces high quality ethanol and concentrated stillage. The invention provides a significant energy savings over conventional bioethanol production and evaporation systems by using the energy that drives the distillation process to also drive a multiple effect evaporator, preferably a multiple effect TASTE™ evaporator (TASTE is a trademark of Benchmark Design LLC of Clearwater, Fla., USA.) to "flash" or evaporate water from the stillage. Additional energy savings are provided by passing fermented material (beer) through one or more pre-heaters of the multiple effect evaporator to increase the temperature of the fermented beer prior to its distillation. The fermented beer also may be passed through a pre-flash or pre-distillation evaporator prior to distillation.

The invention additionally relates to a system ("plant") capable of carrying out at least some aspects of the process described above.

These and other objects, advantages, and features of the invention will become apparent to those skilled in the art from the detailed description and the accompanying drawings. It should be understood, however, that the detailed description and accompanying drawings, while indicating preferred embodiments of the present invention, are given by way of illustration and not of limitation. Many changes and modifications may be made within the scope of the present invention without departing from the spirit thereof, and the invention includes all such modifications.

DETAILED DESCRIPTION OF THE PREFERRED EMBODIMENT

Figure 1:
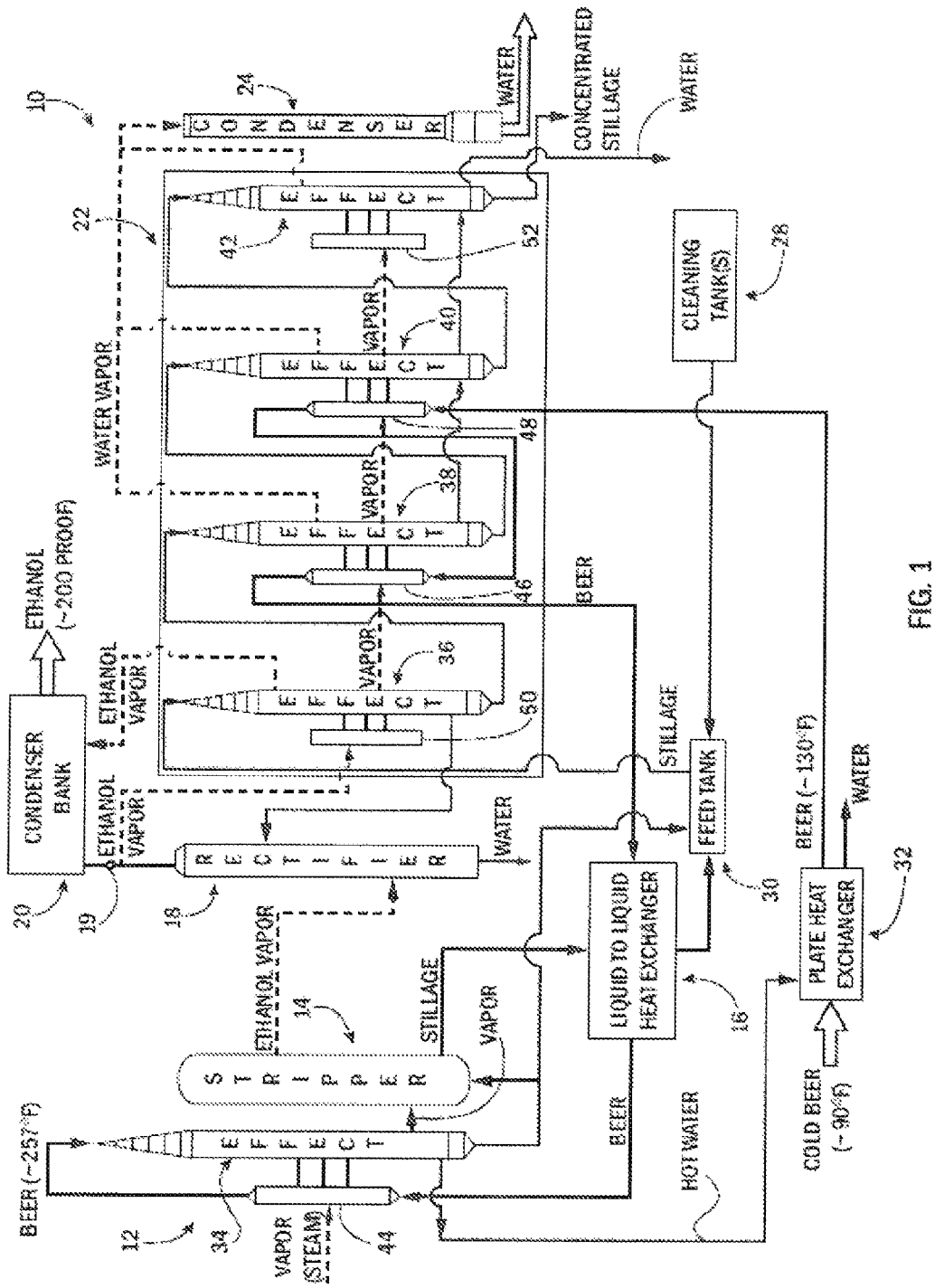
FIG. 1 is a generalize schematic diagram showing the flow of fermented material and vapor through a bioethanol production and evaporation system according to one embodiment of the invention.

Turning now to FIG. 1, a representative bioethanol production system or plant 10 according to one embodiment of the invention is shown. It will be appreciated that several known components of the bioethanol production system 10, such as valves, pumps, and tubing, will not be described with specificity, as such components are generally known.

The absence of any description for these known components in the schematic in no way is intended to limit the disclosure or the scope of the appending claims. It will also be appreciated that certain stages, such as the milling, cooking, and fermentation, have been omitted from the drawings but that the bioethanol production according to the present invention includes, or is otherwise workable with, these known processes. In this regard, the bioethanol production system 10 described herein generally consists of the distillation and condensation stages of a bioethanol production process. Accordingly, one skilled in the art will appreciate that the intake to the bioethanol production system 10 may be fermented feedstock ("beer" or "Vanessa"). The invention is not limited to any type of feedstock. It therefore is used for bioethanol production from e.g. sugarcane, wheat, corn, sugar beet, sorghum, switchgrass, barley, potatoes, sweet potatoes, fruit, and molasses. The invention may also be used for bioethanol production from cellulose.

The bioethanol production system 10 generally includes a pre-flash evaporator 12, a distillation stage, and a post-flash evaporator 22. A liquid-to-liquid heat exchanger 16, a rectifier 18, a condenser bank 20 and a post-evaporator condenser 24 are also provided in this embodiment. In addition to the aforementioned components, the bioethanol production system 10 also has a vacuum pump 26 for pulling a vacuum through the system and one or more cleaning tanks 28 for holding cleaning fluid, which can be pumped through one or more components of the bioethanol production system 10 when cleaning is desired. The bioethanol production system 10 preferably also includes a feed tank (accumulator) 30, described below, as well as a plate-type heat exchanger 32 for preheating the beer, when needed, to a desired temperature, e.g., from 90° F. to 130° F. (32° C. to 54° C.).

In the illustrated embodiment, the pre-flash evaporator 12 is a single effect evaporator, and the post-flash evaporator 22 is four-effect multiple effect evaporator. (An "effect" in this regard is a column where heat energy is used to vaporize at least a portion of an incoming liquid stream. Ancillary equipment associated with a column, such as pumps, valves, a separator, etc., are generally considered part of the effect). However, it is to be understood that the pre-flash evaporator 12 could have two or even more effects. Similarly, the post-flash evaporator 22 could have as few as two effects or as many as nine effects, depending on several factors including designer preference.

The pre-flash evaporator 12 and the post-flash evaporator 22 are preferably each composed of one or more TASTE™ evaporators. The TASTE™ evaporator was originally developed by Gulf Machinery of Clearwater, Fla., the predecessor in interest to Benchmark Design LLC U.S. Pat. No. 6,106,673, the disclosure of which is incorporated herein, also describes a TASTE™ evaporator. The construction and operation of a TASTE™ evaporator are described in greater detail below in connection with FIG. 2.

The pre-flash evaporator 12 of this embodiment has only one effect 34, whereas the multiple-effect evaporator 22 has, four effects 36, 38, 40. 42. However, as discussed briefly above, the pre-flash evaporator 12 also could be a multiple effect evaporator if, for example, more efficient use of the steam that supplies heat energy to the system 10 is desired. Also as discussed above, the post-flash evaporator 22 could have more or fewer than four effects. In the illustrated embodiment, only the first effect 36 of post-flash evaporator 22, handles bioethanol.

Each effect 34, 36, 38, 40, and 42 generally consists of a at least one set of concentric shell-and-tube vessels ("tubenest") that are designed to transfer energy from a saturated vapor stream to "flash" or rapidly vaporize liquid in the tubes as the liquid flows downwardly through the tube and the saturated vapor stream flows upwardly through the surrounding shell. The preferred TASTE™ evaporator is described in more detail below. Mist discharged from the lower end of the tubenest is discharged to a downstream device in the form of either the stripper in the case of the pre-flash evaporator 12 or a separator in the case of each of the effects 36, 38, 40, and 42 of the post-flash evaporator 22.

The distillation stage of this embodiment includes a stripper 14 and a rectifier 18 that cooperate with one another and the remainder of the system as described below.

The pre-flash evaporator 12 and the effects 38 and 40 of the post-flash evaporator 22 have respective pre-heaters 44, 46 and 48. The pre-heater of each evaporator directs the hot vapors or mist for vaporization to the shell of the associated effect and also include a shell and tube heat exchanger in which incoming vapor increases the temperature of a stream of liquid beer flowing through the pre-heater. In the case of the pre-flash evaporator 12, the pre-heater 44 preheats the beer bound for the pre-flash evaporator 12, as will be described more fully below. It is also contemplated that effects 36 and 42 could also be outfitted with pre-heaters if additional preheating of the beer is desired. Effects 36 and 42 have respective vapor distributors 50, 52 that distribute vapor from a separator (not shown) to their respective shells.

Operation of the bioethanol production system 10 will now be described in greater detail with continued reference to FIG. 1. Cold beer, i.e., beer at or below 90° F. (32° C.), is fed under pressure from the feed tanks to a heat exchanger 32, which could be a plate heat exchanger as illustrated or, e.g., a shell and tube heat exchanger. Heat exchanger 32 is designed to increase the temperature of the beer to approximately 130° F. (54° C.) via indirect heat exchange with pressurized hot water being discharged from the shell of the effect 34 of pre-flash evaporator 12 at a temperature of above 240° F. (115° C.) The warmed beer is then pumped successively through pre-heaters 48 and 46 to further raise the temperature of the beer to above 158° F. (70° C.). The beer is then pumped to liquid-to-liquid heat exchanger 16, which further heats the beer by indirect heat exchange with stillage from the stripper 14. After passing through the liquid-to-liquid heat exchanger 16, beer at a temperature above 236° F. (113° C.) is fed to the pre-flash evaporator pre-heater 44, where the beer is heated to a temperature of approximately 257° F. (125° C.) by heat exchangers with water vapor (steam) from a boiler. Using the heat of the pre-heaters 48, 46, 44 to progressively heat the beer effectively uses energy that otherwise would be wasted. The use of stillage from the stripper 14 as the hot liquid source for the liquid-to-liquid heat exchanger 16 provides additional energy savings.

It is noted that additional pre-heaters could be used to provide additional preheating of the beer if necessary, e.g., for incoming cold beer at a temperature below 90° F. For example, instead of or in additional to some or all of the illustrated preheaters, a condensing preheater could be used in the line leading to condenser 24 and/or within the condenser 24. In fact, a preheater could be used at any point in the system where products are being cooled and energy is therefore available for transfer to beer or other products to be warmed.

After the beer is heated to approximately 257° F. (125° C.), the beer is pumped to the upper inlet of the tube of the effect 34 of the pre-flash evaporator 12, whereupon the beer is heated by vapor inbound from the pre-heater 44 and is flash-vaporized as it flows through a nozzle (not numbered) to form a descending turbulent mist. In one implementation, the nozzle provides a 200:1 expansion of the liquid beer. As the misted beer is accelerated along the effect 34, the water vapor is separated from ethanol-laden vapor, leaving a condensed stillage at the bottom of the effect 34. The stillage contains solids, concentrates, and the water that was separated from the alcohol. Depending upon its ethanol content, the stillage may be pumped to the feed tank 30 or to the stripper 14. More particularly, if the stillage contains ethanol, it is fed to the stripper 14, whereas essentially ethanol-free condensate is fed to the feed tank 30 to await further processing in the post-flash evaporator 22. It is also contemplated that the liquid condensate from the pre-flash evaporator 12 could be passed through one or more of the pre-heaters before being fed to the feed tank 30.

Meanwhile, the vapor (steam) in the outer shell of effect 34 condenses to form water that is fed under pressure out of the bottom portion of the effect 34 to the heat exchanger 32. The hot water then is recirculated back to the deareation tank of the boiler.

It should also be noted that, because clean, treated water (either in liquid or vapor form) flows through the boiler, the shell side of the pre-flash evaporator 12, and any downstream equipment such as the plate heat exchanger 32 in a closed loop, little or no make-up water is required for the boiler. This saves considerable expense in terms of water use and water treatment. It also produces considerable energy savings by reducing or eliminating the "preheat load" that otherwise would be required to bring the feed water for the boiler up to or near 212° F. (100° C.).

As noted above, the water vapor and ethanol-laden vapor are separated from the stillage in the pre-flash evaporator 12. The present invention takes advantage of this separation to feed the ethanol-laden vapor collected from the pre-flash evaporator 12 to the stripper 14 and the rectifier 18, where the alcohol and water are separated from one another through differential condensation of the two vapors. In this regard, the flash from the pre-flash evaporator 12 is used as the energy source to drive the stripper 14 and, as will be described, the rectifier 18. Thus, new or "virgin" steam is not needed to drive operation of the stripper 14 and the rectifier 18. Specifically, similar to a conventional distillation process, the ethanol-laden vapor is fed to the stripper 14, which separates the ethanol from the water vapor to produce concentrated ethanol on the order of 60 proof. That is, vapor entrained with ethanol is fed into the stripper 14 near its bottom end. Ethanol vapor and a small amount of water vapor rise out of the the upper outlet of the stripper 14, and the remaining water, possibly having some ethanol entrained with it, is condensed and flows out of the bottom of the stripper 14. Depending on whether or not the resultant stillage has an appreciable percentage of entrained ethanol, it is pumped to either the feed tank 30 for dewatering in the post-flash evaporator 22 or returned to the feed stream entering the inlet of the preheater 44 of the pre-flash evaporator 12.

The ethanol vapor exiting the stripper 14 is directed to the rectifier 18, where it flash vaporizes liquid ethanol refluxed into an upper inlet of the rectifier 18 from the bottom of the first effect 36 of the post flash evaporator 22. Much of the remaining water condenses out of the rectifier 18, venting ethanol vapor that is approximately 120-140 proof. As previously noted, the energy source for the rectifier 18 is the flash vapor, originally from the pre-flash evaporator 12, which has been used to drive the separation process of the stripper 14. Clean water is discharged from the bottom of the rectifier 18. That water may, if desired, be combined with the water exiting the condenser 24.

The approximately 120-140 proof ethanol vapor exiting the upper end of the rectifier 18 could be fed to condenser bank 20 via a valve 19 in a conventional manner. However, the ethanol vapor instead preferably is further dewatered in the post-flash evaporator 22 before being fed to the condenser at about 185-190 proof, and the energy in the incoming ethanol vapor stream preferably is used as the energy source for the effects 36, 38, 40, 42. In this regard, the energy used to drive the stripper 14 and the rectifier 18 also is used to indirectly drive the multiple effect evaporator 22, thereby providing a significant energy savings. That is, no additional steam is needed to drive operation of the multiple effect evaporator 22, which effectively results in stillage dewatering and beer preheating without any additional energy outlay. Hence, the same amount of energy that otherwise would be used for ethanol stripping, i.e., distillation, can now also be used to provide bioethanol, concentrated stillage, and beer preheating. In addition, less heat needs to be removed from the ethanol in the condenser bank 20 to condense the ethanol. In addition, less water needs to be removed from the ethanol in the condenser bank 24, reducing the load on the condenser bank.

The thin stillage from the pre-flash evaporator 12, containing on the order of 85% of separable water by volume, is pumped to the multiple effect evaporator 22, either directly or via the holding tank 30, where the stillage is progressively dewaterd to produce concentrated stillage and pure water. More particularly, a portion of the water in the stillage is evaporated in the first stage effect 36. The stillage is then successively fed to the second, third, and fourth stage effects 38, 40 and 42, respectively, for further dewatering. The concentrated stillage exiting the last effect typically has a reduced water content of about 75%. Further concentration could be achieved by adding additional effects to the evaporator, reducing the water content in the concentrated stillage to 35% or even lower. Energy for this vaporization comes from indirect heat exchange with stream of hot vapors supplied from the adjacent upstream effect (except in the case of the upstream most effect 36 which, as discussed below, receives ethanol vapors from the rectifier 18 as opposed to receiving water vapor from the adjacent upstream effect). In each effect, the stillage becomes progressively more concentrated as a portion of the water is separated from it as a mist. The liquid water in the mist is separated from the vapor stream and returned to the stillage stream, The remaining water vapor stream provides energy for vaporizing more water in the next downstream effect. Vapors are propelled from effect to effect by a progressive reduction in temperature and a resultant reduction in volume and, hence, a reduction of pressure as the vapor moves through the multiple effect evaporator 22. Of the water vapor used to supply energy to the distillate in each effect, a portion condenses and is drawn off as pure water, and the remainder is drawn off via vacuum and condensed in a condenser 24. The condensed water provided by post-evaporator condenser 24 can then be recycled through the production process, e.g., used for mixing with the feedstock prior to fermentation.

As noted above, in a preferred embodiment, each effect of the pre-flash evaporator 12 and post flash evaporator 22 preferably includes a TASTE™ evaporator. A TASTE™ evaporator is characterized by having at least two interrelated parts, namely, 1) a distribution section 54, and 2) a tube bundle or tubenest 56. A liquid vapor separator 58 and preheater 46 may additionally be provided in the effect. These parts can be seen in greater detail in FIG. 2, which shows the second effect 38 of the multiple effect evaporator 22, it being understood that operationally, the same description generally applies generally to the other effects 34, 36, 40, and 42 unless otherwise noted herein. The distribution section 54 includes a distribution cone located above the tubenest 56 and having an expansion nozzle (not shown) disposed at the inlet to the distribution cone. The upper end of the distribution cone has an inlet 55 that is flow-coupled to a supply conduit in a conventional manner to receive distillate from the first effect 36. The nozzle converts at least a substantial portion of the liquid in the distillate to a liquid-vapor mixture by flashing a portion of the liquid into vapor as it expands through the nozzle. The energy for this flash is provided from the evaporated vapor from the upstream effect, The liquid-vapor mix then expands in the distribution cone 54 into a turbulent mist, which fills the distribution cone 54 as it flows downwardly through the cone 54.

The tubenest 56 comprises a shell-and-tube heat exchanger the tubes of which (not shown) receive the mist from the distribution section 54 and the shell of which (not shown) receives vapor from the preceding effect from below. (As noted above, the shell of effect 36 receives vaporized ethanol from the rectifier 18 rather than from an effect.) The turbulent mist from the distribution section 54 thermally accelerates as it flows downwardly through the tubes in the tubenest 56 and absorbs heat through the tube walls from the hot vapors rising upwardly through the adjacent shell toward the upper vapor outlet 57. Because the product falling through the tubes is in the form of a fog or mist, the absorption of heat from the vapor in the shell causes evaporation of about an additional 2% of the entrained water in the mist, which further increases the mist volume. The mist is thus thermally accelerated by continuous adsorption of heat and volumetric expansion of the mist through the entire length of the tubenest 56. Vapor velocity at a lower vapor exit 59 of the tubenest can be as high at near-sonic velocities on the order of as high 400 feet/sec or even higher. The remaining stillage, containing solids and a reduced volume of liquids, exits a bottom liquid outlet 61 of the effect 38.

As noted previously, the effect 38 is associated with a pre-heater 46 that, in addition to heating beer, as described above, also channels the vapor serving as the energy source for flash-vaporization to the shell of the effect 38.

Figure 2:
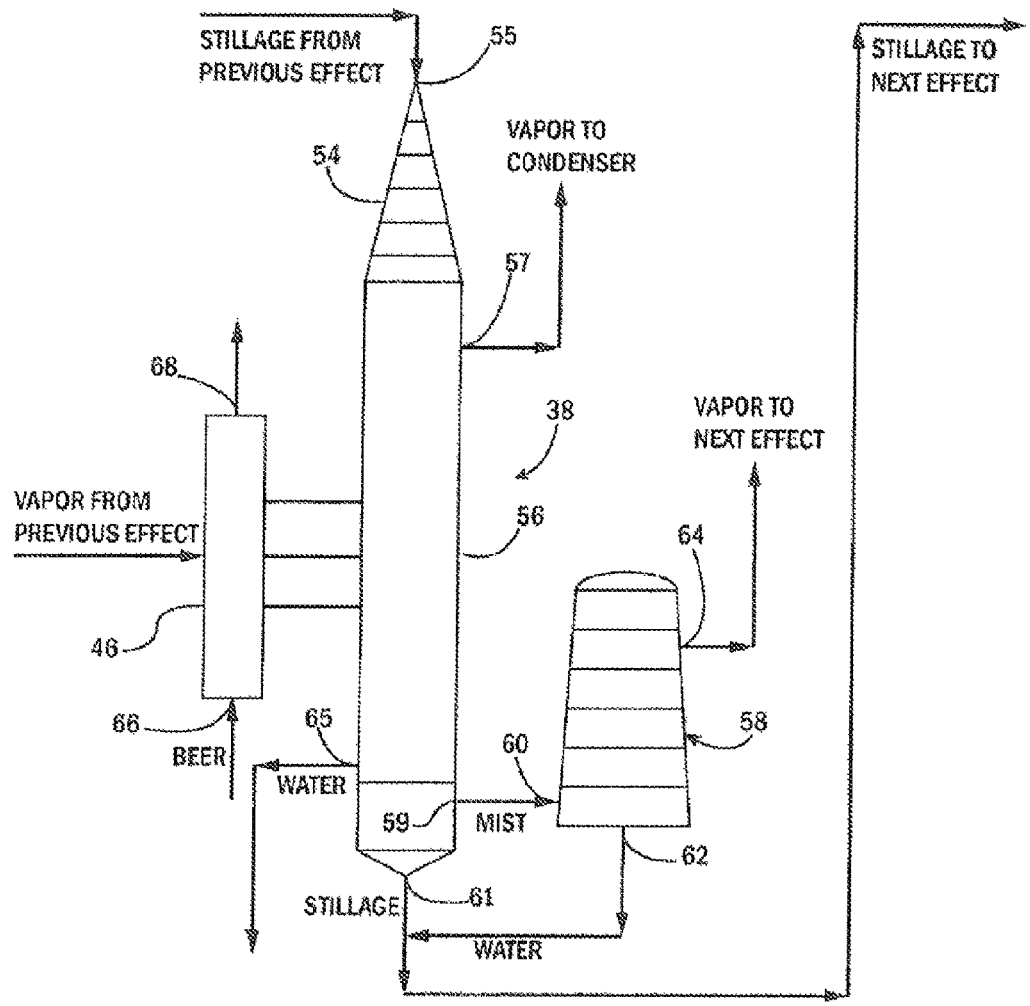
FIG. 2 is an enlarged schematic view of a portion of the schematic diagram of FIG. 1, which shows a multiple effect evaporator of the bioethanol production and evaporation system of the present invention.

Still referring to FIG. 2 by way of example, each effect has a separator 58 that provides liquid/vapor separation of the stream leaving the bottom of the tubenest. The separator 58 may be in the form of dry wall separator or a centrifugal vapor-liquid separator having an inlet 60 which receives vapor leaving the bottom of the preceding tubenest, i.e., the tubenest of effect 36 in the ease of effect 38. The illustrated drywall separator 58 uses the high-velocities of the vapor to divide the mixture into vapor and liquid components from the preceding effect in a manner that is generally well known. The concentrated liquid drains from an outlet 62 into the suction side of a pump (not numbered) and is combined with the stillage flowing out of the bottom of the corresponding effect and pumped into the upper inlet of the next downstream effect (effect 40 in the case of effect 38). The vapor from the separator 58 is discharged from an outlet 64 of the separator 58 and directed to the next downstream effect, where it serves as the energy source for that effect.

With reference briefly again to FIG. 1, it is noted that the pre-flash evaporator 12 does not have the aforedescribed separator. The combined water/alcohol stream instead is directed to the stripper 14. However, a separator could be used with some types of strippers, and a separator preferably would be provided between the effects of a multiple effect pre-flash evaporator.

Some of the vapor supplied to the shell of each effect condenses during this process and flows out of a bottom outlet 65 of the effect. In the case of effect 36, in which the vapor in the shell comprises ethanol, the liquid ethanol is refluxed or pumped back to an upper inlet of the rectifier 18 as described above. In the case of the remaining effects 38, 40, and 42 in which the vapor in the shell is water, the condensed water flowing out of the bottom of the effect is pumped through the bottom(s) of the remaining downstream effect(s) and ultimately discharged from the system 10.

Turning again to FIG. 2, in a preferred embodiment, the pre-heater 46 of effect 36 has a beer inlet 66 at its lower end and a beer outlet 68 at its upper end. In this regard, the beer is heated by the pre-heater 46 as it travels along the body of the pre-heater between the beer inlet and beer outlet. Thus, the pre-heater 46 provides heating of the beer that is passed therethrough but also provides heat to the incoming vapor for subsequent use during water evaporation from the distillate. As noted previously, in a preferred but not limited embodiment, effects 36, 42 have vapor distributors that provide heat to the vapor fed thereto for evaporation but are not used to apply heat to the beer.

It is believed that a multiple effect TASTE™ evaporator provides substantial benefits over conventional dewatering systems for removing water from the distillate. For instance, the outputs of the multiple effect TASTE™ evaporator generally consists of a concentrated stillage and high quality, i.e., pure, water. As noted above, it is not uncommon for a system to pump 280,000 pounds of thin stillage per hour. The present invention is able segment that volume of pumped fluid into constituent components; namely, approximately 40,000 pounds of concentrated stillage and 240,000 pounds of water per hour.

The invention is not limited to such ratios, but these values show but one example of the improvements the present invention provides in processing the distillate from bioethanol production. The relatively high quality water can then be recycled back through the system and used for cooking or fermentation, or used for irrigation. The concentrated stillage, having about 85% of its total water content removed and now containing about 75% water, can be treated and used as a nutrient rich concentrated liquid fertilizer. It could be dried and further processed or missed for use as a solid fertilizer, livestock dressing, and the like.

Additionally, while a preferred embodiment of the invention is to substantially dewater the distillate, it is understood that the bioethanol production system 10 could be set up so that a reduced watered distillate, rather than a dewatered distillate, is collected. For example, it is contemplated that the system could be set up to provide ethanol and a flowable syrup or molasses.

I claim:

1. An ethanol production system comprising:
    a pre-flash stage that flashes a fermented liquid to form an, ethanol-laden vapor and a substantially ethanol-free liquid;
    a distillation stage that distils ethanol from the ethanol-laden vapor; and
    a post-flash stage that removes water from the substantially ethanol-free liquid to provide a concentrated stillage.

2. The system of claim 1, wherein the vapor from the pre-flash stage is fed to the distillation stage, and wherein the distillation stage includes at least a stripper and a rectifier.

3. The system of claim 2, wherein ethanol from the vapor is fed to the post-flash stage as an energy source for the post-flash stage.

4. The system of claim 1, wherein the pre-flash stage includes a pre-distillation evaporator comprising an effect that includes an expansion cone containing an internal expansion nozzle.

5. The system of claim 4, wherein the expansion nozzle causes liquid to vaporize and to expand at a ratio of approximately 200:1.

6. The system of claim 4, wherein the pre-distillation evaporator comprises at least two effects, each of which includes an expansion cone containing an internal expansion nozzle.

7. The system of claim 1, wherein the post-flash stage includes a multiple effect evaporator having multiple effects, each having an expansion cone containing an internal expansion nozzle.

8. The system of claim 7, wherein each expansion nozzle causes liquid to vaporize and to expand at a ratio of approximately 200:1.

9. The system of claim 1, further comprising one or more pre-heaters, and wherein the fermented liquid is passed through the one or more pre-heaters before being fed to the pre-flash stage to raise the temperature of the fermented liquid to approximately 257° F. (125° C.).

10. A process of producing ethanol and concentrated stillage from a fermented product, comprising:
    flashing the fermented product in an evaporator to produce an ethanol-laden vapor, water vapor, and stillage, the evaporator being a thermally accelerating evaporator having an upper distribution section having an internal expansion nozzle and a tubenest located beneath the distribution section;
    feeding the ethanol-laden vapor and the water vapor to a distilling assembly; and
    evaporating water from the stillage using a thermally accelerating evaporator to reduce the water content of the stillage.

11. The process of claim 10, wherein, during the flashings step, the product expands at a ratio of approximately 200:1.

12. An ethanol production system comprising:
    a distillation stage that distills ethanol from a fermented liquid and that discharges stillage;
    an evaporation stage that dewaters stillage from the distillation stage;
    at least one preheater, associated with the evaporation stage, which provides heated vapor to the evaporation stage and further provides heat to the fermented liquid before the fermented liquid is input to the distillation stage.

13. The system of claim 12, wherein the evaporation stage includes an effect including a thermally accelerating evaporator having an expansion cone containing an internal expansion nozzle.

14. The system of claim 13, wherein the expansion nozzle causes liquid to vaporize and to expand at a ratio of between 100:1 and 300:1.

15. The system of claim 13, wherein the thermally accelerating evaporator is a multiple effect evaporator.

16. The system of claim 12, further comprising a pre-distillation evaporator through which the fermented liquid is passed prior to being fed to the distillation stage.

17. The system of claim 16, wherein the pre-distillation evaporator comprises an effect including a thermally accelerating evaporator having a pre-heater.

18. The system of claim 17, wherein the pre-distillation evaporator has at least two effects, each including a thermally accelerating evaporator having a pre-heater.

19. The system of claim 17, wherein the pre-heater of the pre-distillation evaporator provides heat to the fermented liquid before the fermented liquid is input to the distillation stage.

* * * * *